US012564544B2

(12) United States Patent
Nemitz et al.

(10) Patent No.: US 12,564,544 B2
(45) **Date of Patent: *Mar. 3, 2026**

(54) THICKENED ALKALYZATION COMPONENT FOR OXIDATIVE HAIR LIGHTENING PRODUCT

(71) Applicant: Henkel AG & Co. KGaA, Duesseldorf (DE)

(72) Inventors: Oliver Nemitz, Duesseldorf (DE); Anja Reichert, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 585 days.

This patent is subject to a terminal disclaimer.

(21) Appl. No.: 18/002,033

(22) PCT Filed: Jun. 7, 2021

(86) PCT No.: PCT/EP2021/065136

§ 371 (c)(1),
(2) Date: Dec. 15, 2022

(87) PCT Pub. No.: WO2021/254803

PCT Pub. Date: Dec. 23, 2021

(65) Prior Publication Data

US 2023/0338255 A1 Oct. 26, 2023

(30) Foreign Application Priority Data

Jun. 17, 2020 (DE) ..................... 10 2020 207 461.5

(51) Int. Cl.

| | |
|---|---|
| ***A61K 8/41*** | (2006.01) |
| ***A61K 8/22*** | (2006.01) |
| ***A61K 8/365*** | (2006.01) |
| ***A61K 8/60*** | (2006.01) |
| ***A61K 8/73*** | (2006.01) |
| ***A61Q 5/08*** | (2006.01) |

(52) U.S. Cl.

CPC .................. *A61K 8/41* (2013.01); *A61K 8/22* (2013.01); *A61K 8/365* (2013.01); *A61K 8/602* (2013.01); *A61K 8/731* (2013.01); *A61Q 5/08* (2013.01)

(58) Field of Classification Search

CPC ....................................................... A61K 8/00
USPC ............................................................ 8/405
See application file for complete search history.

(56) References Cited

U.S. PATENT DOCUMENTS

2006/0117494 A1* 6/2006 Marsh .................... A61K 8/416 8/405

FOREIGN PATENT DOCUMENTS

| | | | |
|---|---|---|---|
| WO | 2015028015 | A1 | 3/2015 |
| WO | 2017008949 | A1 | 1/2017 |
| WO | 2020064270 | A1 | 4/2020 |

* cited by examiner

*Primary Examiner* — Walter E Webb
(74) *Attorney, Agent, or Firm* — Ingrassia Fisher & Lorenz, LLP

(57) ABSTRACT

The present disclosure relates to a water-based cosmetic composition thickened with xanthan gum and sodium carboxymethyl cellulose, having a strongly alkaline pH, to be used as an alkalizing component in a two- or three-part oxidative hair lightening agent.

17 Claims, No Drawings

THICKENED ALKALYZATION COMPONENT FOR OXIDATIVE HAIR LIGHTENING PRODUCT

CROSS-REFERENCE TO RELATED APPLICATION

This application is a U.S. National-Stage entry under 35 U.S.C. § 371 based on International Application No. PCT/EP2021/065136, filed Jun. 7, 2021, which was published under PCT Article 21(2) and which claims priority to German Application No. 102020207461.5, filed Jun. 17, 2020, which are all hereby incorporated in their entirety by reference.

TECHNICAL FIELD

The present disclosure relates to a water-based cosmetic composition thickened with xanthan gum and sodium carboxymethyl cellulose, having a strongly alkaline pH, to be used as an alkalizing component in a two- or three-part oxidative hair lightening agent. Furthermore, the present disclosure relates to a kit comprising said alkalizing component and a hair lightening method using said alkalizing component.

BACKGROUND

In addition to coloring, the lightening of one's own hair color or bleaching is a wish of many consumers, as a blonde hair color is regarded as attractive and desirable in terms of fashion. If hair is to be lightened or even bleached, the natural colorants responsible for the natural color of the hair, especially the body's own melanins eumelanin and phaeomelanin, are broken down oxidatively using oxidizing agents, such as hydrogen peroxide in particular, and the hair is thus decolorized and lightened or even bleached.

To develop an optimal brightening performance of the oxidant, oxidative brightening agents require an alkaline pH value for reaction acceleration, especially in the range of pH 10.0 to 11.0. However, hydrogen peroxide, the oxidizing agent most commonly used for cosmetic purposes, can only be stored at low pH values, i.e. in the range of pH 2.0 to 6.5. Therefore, commercially available bleaching agents are usually packaged as a kit comprising an aqueous hydrogen peroxide solution with a more acidic pH value, preferably in the range of pH 2.0 to 6.5, and an alkalizing component. Both components are only mixed together shortly before application to the hair. The composition and mixing ratio of the two components are matched to one another in such a way that the resulting application mixture has an alkaline pH value, in particular in the range of pH 9 to 10. In addition, a persulfate-comprising composition—usually anhydrous—can be added to the alkaline hydrogen peroxide-comprising application mixture shortly before application to the hair to enhance the lightening effect of the bleaching agent. Such a commercially available bleaching agent is available as a kit comprising an aqueous hydrogen peroxide solution with a more acidic pH, preferably in the range of pH 2.0 to 6.5, an—often creamy—alkalizing component and an anhydrous persulfate-comprising composition. Often the kits described above also contain one or more portions of a hair conditioner for the nourishing after-treatment of the hair after the completed bleaching treatment.

The application time for attractive whitening results is usually in the range of 5 to 60 minutes. It is therefore necessary that the individual components of the ready-to-use bleaching agent are formulated in such a way that on the one hand they can be mixed well with each other and then distributed on the hair to be bleached and on the other hand they are sufficiently viscous to remain on the hair to be bleached during the application time without dripping down. This viscosity can be adjusted by polymeric thickeners, and this thickener can be included in both the alkalizing component and the oxidizer preparation, as well as in the optional anhydrous persulfate-comprising composition.

The alkaline pH of the alkalizing component is adjusted with alkalizing agents, mainly ammonium hydroxide or ammonia water or alkanolamines as well as mixtures of these alkalizing agents. Ammonium hydroxide and alkanolamines, especially monoethanolamine, are particularly good for swelling the cuticle, i.e. the outer cuticle layer of the keratin fiber, so that the oxidizing agent can penetrate well into the keratin fiber and lighten it. Basic amino acids and inorganic bases are less suitable as sole alkalizing agents; however, these components can be used as additional alkalizing agents.

To produce the ready-to-use bleaching agent, the alkalizing component is usually mixed with an aqueous hydrogen peroxide solution to form a homogeneous cream or gel and applied directly afterwards to the hair to be lightened. Optionally, an anhydrous persulfate-comprising composition can be added to this mixture to further enhance the lightening and bleaching performance of the agent. This bleaching agent remains on the hair for a period of 5 to 60 minutes until the oxidative degradation of the natural melanin hair colorants, i.e. eumelanin and pheomelanin, is completed to the desired extent. The bleaching agent is then washed out of the hair. The degree of melanin degradation and thus the achieved lightening of the hair depends on various properties of the hair, in particular on the original amount of the black-brown pigment eumelanin and the red-gold pigment phaeomelanin as well as on the structure of the hair fibers. A good bleaching agent is able to break down melanin as completely as possible while not creating undesirable shades. Furthermore, it is important to achieve a lightening result that is as uniform as possible along the keratin fiber, which is independent of the degree of damage to the keratin fiber along its length. This means that on the less damaged hair near the hairline or the hair root the same color tone is achieved as possible as on the more damaged hair tip. This property of the bleaching agent is also called leveling capacity.

The alkalizing agent or mixture of alkalizing agents is usually incorporated into a cosmetically suitable carrier, such as a cream or gel. The carrier ensures a homogeneous distribution and a sufficient residence time of the hair whitening agent on the hair. The alkalizing component of an oxidative hair lightener is often referred to as a bleaching cream. Fat components with a melting point above 30° C. often serve as consistency agents for creams. These include in particular higher linear fatty alcohols, such as myristyl alcohol, cetyl alcohol and stearyl alcohol, and polyol esters, such as glyceryl monostearate, glyceryl distearate, ethylene glycol monostearate and ethylene glycol distearate, but also wax esters, such as cetyl palmitate and myristyl myristate, and hydrogenated oils, e.g. hydrogenated castor oil.

A disadvantage is the complex production of such a cream, which comprises higher-melting consistency agents. A lot of energy is required to melt the fat components and emulsify them with the water phase. The subsequent cooling process consumes large amounts of cooling water.

Instead of or in addition to higher-melting fat-based consistency agents, thickening can also be achieved by employing a polymer thickener. Corresponding alkalizing components of the prior art contain for this purpose polymers or copolymers with acrylate-, methacrylate- or vinyl-comprising monomers, e.g. carbomer, sodium polyacrylates, PVP, amphiphilic polyacrylate copolymers, such as copolymers with the INCI designations Acrylates/C10-30 Alkyl Acrylate Cross polymer and Acrylates/Steareth-20 Methacrylate Copolymer, or polyurethanes, e.g. PEG-150/Decyl Alcohol/SMDI Copolymer. Such polymers and copolymers are hydrophilic or amphiphilic and form a gel skeleton in the alkaline aqueous phase. Due to their persistence in the environment, the use of such polymers should be avoided wherever possible. Products with such ingredients are classified in water hazard class 2 (WGK 2), i.e. as "clearly hazardous to water".

Another disadvantage of alkalizing components thickened with a vinyl, acrylate or polyurethane polymer is that the gels can swell considerably during prolonged storage. This can occur if the consumer does not immediately use up the entire application mixture comprising alkalizing component (M1), oxidizing agent preparation (M2) and, if necessary, Blond booster composition (M3), but stores the residual quantity in the sealed mixing bottle for several days—contrary to the recommended instructions for use. This increases their volume, which inflates the storage bottles and, in the worst case, can cause them to burst.

Another disadvantage of alkalizing components thickened with a vinyl, acrylate or polyurethane polymer is that the texture of the gels can sometimes have a detrimental effect on the spread ability of the product on the hair.

BRIEF SUMMARY

This disclosure provide an alkalizing component for an oxidative hair lightening agent, comprising

- about 81-92 about wt. % water,
- about 1-about 2 wt. % xanthan gum,
- about 0.5-about 1.5 wt. % sodium carboxymethyl cellulose,
- at least one alkalizing agent selected from ammonium hydroxide and alkanolamines and mixtures thereof, in a total amount of about 3-about 9 wt. %,
- at least one oil in a total amount of about 0.5-about 7.0 wt. %,
- at least one surfactant selected from anionic, zwitterionic, amphoteric and alkyl oligoglycoside surfactants substituted with at least one C8 to C14 alkyl radical, in a total amount of about 0.4-about 2 wt. %,
- about 0-about 0.1 wt. % peroxide,
- where all figures in % by weight are based on the weight of the alkalizing component,
- wherein the alkalizing component has a pH in the range of about 8.0 to about 12.0 measured at about 20° C.,
- where no percarbonate is present,
- wherein no polymer or copolymer with acrylate-, methacrylate- or vinyl-containing monomers and no polyurethane is present, and
- wherein no fat component having a melting point of about 28° C. or higher is included.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description. It is to be appreciated that all numerical values as provided herein, save for the actual examples, are approximate values with endpoints or particular values intended to be read as "about" or "approximately" the value as recited.

Consequently, the present disclosure was based on the tasks of providing a thickened alkalizing component for an oxidative hair lightening agent, which leads to improved whitening results, in particular with respect to the amount of oxidant required, and the uniformity of the lightening along the keratin fiber (leveling), is more environmentally friendly in the production as well as in the selection of ingredients, is easier to distribute on the hair.

These tasks are solved by an alkalizing component for an oxidative hair lightening agent, comprising

- 81-92 wt. % water,
- 1-2 wt. % xanthan gum,
- 0.5-1.5 wt. % sodium carboxymethyl cellulose,
- at least one alkalizing agent selected from ammonium hydroxide and alkanolamines and mixtures thereof, in a total amount of 3-9 wt. %,
- at least one oil in a total amount of 0.5-7.0 wt. %, preferably 2.0 to 5.5 wt. %, more preferably 3.5 to 5.0 wt. %,
- at least one surfactant selected from anionic, zwitterionic, amphoteric and alkyl oligoglycoside surfactants substituted with at least one C8 to C14 alkyl radical, in a total amount of 0.4-2 wt. %,
- 0-0.1 wt. % peroxide,
- where all figures in % by weight are based on the weight of the alkalizing component,
- wherein the alkalizing component has a pH in the range of 8.0 to 12.0, preferably in the range of 9.6 to 11.5, particularly preferably in the range of 10.0 to 11.0, measured at 20° C.,
- where no per carbonate is present,
- wherein no polymer or copolymer with acrylate-, methacrylate- or vinyl-comprising monomers and no polyurethane is present, and
- wherein no fat component having a melting point of 28° C. or higher is included.

The alkalizing component as contemplated herein comprises, in each case based on its weight, water in an amount of 81-92 wt. %, preferably 82-89 wt. %, particularly preferably 83-86 wt. %.

The alkalizing component as contemplated herein comprises, in each case based on its weight, xanthan gum in an amount of 1-2 wt. %, preferably 1.2-1.8 wt. %, particularly preferably 1.5-1.7 wt. %.

The alkalizing component as contemplated herein comprises, in each case based on its weight, sodium carboxymethylcellulose in an amount of 0.5-1.5 wt. %, preferably 0.7-1.1 wt. %, particularly preferably 0.8-0.9 wt. %.

Alkalizing components preferred as contemplated herein are exemplified by the fact that, apart from xanthan gum and sodium carboxymethyl cellulose, no other polysaccharide is present.

The alkalizing component as contemplated herein comprises, in each case based on its weight, at least one alkalizing agent selected from ammonium hydroxide and alkanolamines and mixtures thereof, in a total amount of 2-9 wt. %, preferably in a total amount of 3-8 wt. %, particularly preferably in a total amount of 4-7.5 wt. %.

Alkalizing components preferred as contemplated herein contain, in each case based on their weight, 3-5 wt. %, preferably 3.5-4 wt. % ammonium hydroxide.

Alkanolamines which can be used as alkalizing agents as contemplated herein are preferably selected from primary amines having a C2-C6 alkyl parent carrying at least one hydroxyl group. Particularly preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, and mixtures thereof. Alkanolamines which are very particularly preferred as contemplated herein are selected from the group of 2-aminoethan-1-ol, 2-amino-2-methylpropan-1-ol and 2-amino-2-methylpropane-1,3-diol and mixtures thereof. An exceptionally preferred alkanolamine as contemplated herein is 2-aminoethan-1-ol (monoethanolamine).

Alkalizing components preferred as contemplated herein contain at least one alkanolamine selected from primary amines having a C2-C6 alkyl parent carrying at least one hydroxyl group in a total amount of 2-9 wt. %, preferably 3-8 wt. %, particularly preferably in a total amount of 4-7.5 wt. %, in each case based on their weight.

Further alkalizing components preferred as contemplated herein contain at least one alkanolamine selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, and mixtures thereof, in a total amount of 2-9 wt.-%, preferably 3-8 wt. %, particularly preferably in a total amount of 4-7.5 wt. %, in each case based on their weight.

Further alkalizing components preferred as contemplated herein contain, in each case based on their weight, 2-9 wt. %, preferably 3-8 wt. %, particularly preferably 4-7.5 wt. % 2-aminoethan-1-ol (monoethanolamine).

The choice of alkalizing agent depends on the desired degree of brightening. For a particularly high degree of brightening, a mixture of ammonium hydroxide and at least one alkanolamine is selected as alkalizing agent in a total amount of 4-9 wt. %, preferably 5-8 wt. %, particularly preferably 6-7 wt. %, in each case based on the weight of the alkalizing component.

A mixture of ammonium hydroxide and 2-aminoethan-1-ol (monoethanolamine) in a total amount of 4-9 wt. %, preferably 5-8 wt. %, particularly preferably 6-7 wt. %, in each case based on the weight of the alkalizing component, is preferred.

Furthermore, the alkalizing component as contemplated herein comprises, in each case based on its weight, at least one oil in a total amount of 0.5-7.0 wt. %, preferably 2.0 to 5.5 wt. %, particularly preferably 3.5 to 5.0 wt. %. The addition of an oil in the specified amounts supports the leveling ability of the bleaching agent, thus ensuring an even lightening result, regardless of the degree of damage along the keratin fiber. In addition, the oil optimizes the texture of the alkalizing component of the present disclosure.

Alkalizing components preferred as contemplated herein are exemplified in that the at least one oil is selected from branched, saturated fatty alcohols having 6-30 carbon atoms and from the esters of saturated, linear or branched fatty alcohols having 2-30 carbon atoms with saturated, linear or branched fatty acids having 2-30 carbon atoms, which may be hydroxylated, and mixtures thereof.

The branched alcohols are often referred to as Guerbet alcohols because they are available after the Guerbet reaction. Preferred branched, saturated fatty alcohols with 6-30 carbon atoms are 2-hexyldecanol, 2-octyldodecanol, 2-ethylhexyl alcohol and isostearyl alcohol, and mixtures thereof. Exceptionally preferred is 2-octyldodecanol.

Other oils particularly preferred as contemplated herein are selected from the esters of saturated, linear or branched fatty alcohols having 2-30 carbon atoms with saturated, linear or branched fatty acids having 2-30 carbon atoms, which may be hydroxylated. These preferably include cetyl 2-ethylhexanoate, 2-hexyldecyl stearate, 2-hexyldecyl laurate, isodecyl neopentanoate, isononyl isononanoate, 2-ethylhexyl palmitate, 2-ethylhexyl stearate, isopropyl myristate, isopropyl palmitate, isopropyl stearate, isopropyl isostearate, isooctyl stearate, isononyl stearate, isocetyl stearate, isononyl isonanoate, isotridecyl isononanoate, cetearyl isononanoate, 2-ethylhexyl laurate, 2-ethylhexyl isostearate, 2-ethylhexyl cocoate, 2-octyl dodecyl palmitate, butyloctanoic acid 2-butyloctanoate, diisotridecyl acetate, n-butyl stearate and n-hexyl laurate, and mixtures thereof.

Alkalizing components which are particularly preferred as contemplated herein are exemplified in that the at least one oil is selected from 2-hexyldecanol, 2-octyldodecanol, 2-ethylhexyl alcohol, isostearyl alcohol, cetyl 2-ethylhexanoate, 2-hexyldecyl stearate, 2-hexyldecyl laurate, isodecyl neopentanoate, isononyl isononanoate, 2-ethylhexyl palmitate, 2-ethylhexyl stearate, isopropyl myristate, isopropyl palmitate, isopropyl stearate, isopropyl isostearate, isooctyl stearate, isononyl stearate, isocetyl stearate, isononyl isononanoate, isotridecyl isononanoate, cetearyl isononanoate, 2-ethylhexyl laurate-, 2-ethylhexyl isostearate, 2-ethylhexyl cocoate, 2-octyldodecyl palmitate, butyloctanoic acid 2-butyloctanoate, diisotridecyl acetate, n-butyl stearate and n-hexyl-laurate, and mixtures thereof. Extremely preferred alkalizing components as contemplated herein are exemplified in that they contain, by weight, 0.5-7.0 wt. %, preferably 2.0 to 5.5 wt. %, particularly preferably 3.5 to 5.0 wt. %, of 2-octyldodecanol.

Furthermore, the alkalizing component as contemplated herein comprises, in each case based on its weight, at least one surfactant selected from anionic, zwitterionic, amphoteric and alkyl oligoglycoside surfactants substituted with at least one C8 to C14 alkyl radical, in a total amount of 0.4-2 wt. %, preferably 0.7-1.3 wt. %. Such a surfactant is required, on the one hand, to emulsify the at least one oil in a storage-stable manner and, on the other hand, to facilitate the washing of the hair lightening agent out of the hair.

Anionic Surfactant

Suitable anionic surfactants are all anionic surface-active substances suitable for use on the human body which have a water-solubilizing anionic group, for example a carboxylate, sulfate, sulfonate or phosphate group, and a lipophilic alkyl group with 8 to 14 C atoms, preferably 8 to 12 C atoms, in the molecule. In addition, glycol or polyglycol ether groups, ester, ether and amide and hydroxyl groups may also be present in the molecule. Examples of suitable anionic surfactants are, in each case in the form of the sodium, potassium and ammonium as well as the mono, di and trialkanolammonium salts with 2 to 4 C atoms in the alkanol group, linear and branched fatty acids with 8 to 14 C atoms (soaps), polyethoxylated ether carboxylic acids, acyl sarcosides, acyl taurides, acyl isethionates, sulfosuccinic acid mono- and dialkyl esters and sulfosuccinic acid mono-alkyl polyoxyethyl esters comprising 1 to 6 ethylene oxide groups, linear alkane sulfonates, linear alpha-olefin sulfonates, sulfonates of unsaturated fatty acids with up to 6 double bonds, alpha-sulfofatty acid methyl esters of fatty acids, $C_8$-$C_{14}$ alkyl sulfates and $C_8$-$C_{14}$ alkyl ether sulfates with up to 15 oxyethyl groups, mixtures of surface-active hydroxysulfonates, sulfated hydroxyalkyl polyethylene and/or hydroxyalkylene propylene glycol ethers, esters of tartaric acid or citric acid with ethoxylated or propoxylated fatty alcohols, optionally polyethoxylated alkyl and/or alkenyl ether phosphates, sulfated fatty acid alkylene glycol esters, and monoglyceride sulfates and monoglyceride ether sulfates. Preferred anionic surfactants are $C_8$-$C_{14}$ alkyl sulfates, $C_8$-$C_{14}$ alkyl ether sulfates and $C_8$-$C_{14}$ ether carboxylic acids with 8 to 14 C atoms in the alkyl group and up to 12 ethylene oxide groups in the molecule. Preferred alkalizing components contain, by weight, at least one anionic surfactant in a total amount of 0.4-2 wt. %, preferably 0.7-1.3 wt. %. Sodium laureth(2) sulfate is particularly preferred. Exceptionally preferably, based on the weight of the alkalizing component, 0.4-2 wt. %, preferably 0.7-1.3 wt. % sodium laureth(2) sulfate is present.

Zwitterionic Surfactant

The term zwitterionic surfactants is used to describe surface-active compounds which, in addition to at least one lipophilic alkyl group comprising 8 to 14 carbon atoms, preferably 8 to 12 carbon atoms, carry in the molecule at least one quaternary ammonium group and at least one carboxylate, sulfonate or sulfate group. Particularly suitable zwitterionic surfactants are the so-called betaines such as the N-alkyl-N,N-dimethylammonium glycinates, for example cocoalkyl dimethylammonium glycinate, N-acyl-aminopropyl-N,N-dimethylammonium glycinate, for example cocoacylaminopropyl dimethylammonium glycinate, and 2-alkyl-3-carboxymethyl-3-hydroxyethyl imidazolines each having 8 to 18 carbon atoms in the alkyl or acyl group, and cocoacylaminoethyl hydroxyethyl carboxymethyl glycinate. A preferred zwitterionic surfactant is the fatty acid amide derivative known under the INCI designation cocamidopropyl betaine. Preferred alkalizing components contain, by weight, at least one zwitterionic surfactant in a total amount of 0.4-2 wt. %, preferably 0.7-1.3 wt. %.

Amphoteric Surfactant

Amphoteric surfactants are surface-active compounds which, apart from a $C_8$-$C_{14}$ alkyl or acyl group, contain at least one free amino group and at least one —COOH or —$SO_3H$ group in the molecule and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having about 8 to 24 carbon atoms in the alkyl group. Particularly preferred amphoteric surfactants are N-Cocoalkylaminopropionate, Cocoacylaminoethylaminopropionate and $C_{12}$-$C_{18}$ Acylsarcosine. Preferred alkalizing components contain, by weight, at least one amphoteric surfactant in a total amount of 0.4-2 wt. %, preferably 0.7-1.3 wt. %.

Alkyl Oligoglycoside Surfactant

Other preferred surfactants are selected from $C_8$-$C_{14}$ alkyl oligoglycosides. $C_8$-$C_{14}$ alkyl oligoglycosides represent well-known, commercially available surfactants. They are produced in particular by reacting glucose or oligosaccharides with primary alcohols comprising 8-14 carbon atoms. With regard to the glycoside residue, monoglycosides in which a cyclic sugar residue is glycosidically bonded to the fatty alcohol as well as oligomeric glycosides with a degree of oligomerization of up to about 8, preferably 1-2, are suitable. The degree of oligomerization is a statistical mean value based on a homologue distribution that is common for such technical products. Products available under the trademark Plantacare® contain a glucosidically bonded $C_8$-$C_{14}$ alkyl group on an oligoglucoside residue whose average degree of oligomerization is 1-2, in particular 1.2-1.4. Particularly preferred $C_8$-$C_{14}$ alkyl oligoglycosides are selected from octyl glucoside, decyl glucoside and lauryl glucoside, and mixtures thereof. Preferred alkalizing components contain, by weight, at least one $C_8$-$C_{14}$ alkyl oligoglycoside in a total amount of 0.4-2 wt. %, preferably 0.7-1.3 wt. %. As contemplated herein, alkyl oligoglycoside surfactants are not considered polysaccharides.

The obligatory feature "0-0.1 wt. % peroxide" is intended to express that the alkalizing component as contemplated herein is the peroxide-free component of an oxidative hair lightening agent prior to preparation of the hair lightening agent ready for use. Small amounts of peroxide, which could be introduced by appropriate pretreatment of the water used for production, are considered acceptable. A peroxide content of up to 0.1 wt. %, based on the weight of the alkalizing component, does not yet lighten the hair.

The alkalizing component as contemplated herein has a pH in the range from 8.0 to 12.0, preferably in the range from 9.6 to 11.5, particularly preferably in the range from 10.0 to 11.0, in each case measured at 20° C.

The alkalizing component as contemplated herein comprises no percarbonate, i.e., based on its weight, 0.0 wt. % percarbonate.

The alkalizing component as contemplated herein comprises no polymer or copolymer with acrylate-, methacrylate- or vinyl-comprising monomers and no polyurethane, i.e., based on its weight, 0.0 wt. % of the aforementioned (co-)polymers.

The alkalizing component as contemplated herein does not contain any fatty component with a melting point of 28° C. or higher, in particular fatty components with a melting point in the range from 28° C. to 300° C. Examples of such fat components undesirable as contemplated herein are linear, saturated 1-alkanols with at least 14 carbon atoms, such as 1-tetradecanol (myristyl alcohol), 1-hexadecanol (cetyl alcohol), 1-octadecanol (stearyl alcohol) and 1-icosanol (arachyl alcohol), waxes, such as beeswax or kerosene wax, esters of glycerol, 1,2-propylene glycol or of ethylene glycol, such as glyceryl monostearate, glyceryl distearate, hydrogenated castor oil, propylene glycol distearate, ethylene glycol monostearate or ethylene glycol distearate.

Alkalizing components preferred as contemplated herein are exemplified by having a viscosity in the range from 2,000 to 110,000 mPa-s, preferably 40,000 to 100,000 mPa-s, particularly preferably 70,000 to 90,000 mPa-s, in each case measured at 20° C.

The parameters for the viscosity measurements are: Device: Brookfield viscometer RDV-II+; temperature: 20° C.; spindle 5; shear rate: 4 revolutions per minute (4 RPM).

These viscosities are excellent for handling this agent itself (preparation, dosing to prepare the mixture with the oxidant preparation and, if necessary, the Blond booster).

Surprisingly, it was found that the leveling properties of a blonding agent based on an alkalizing component preferred as contemplated herein could be further improved by the addition of glucoheptonic acid and/or at least one of its physiologically tolerated salts and/or lactones.

Alkalizing components preferred as contemplated herein are exemplified in that glucoheptonic acid and/or at least one of its physiologically compatible salts and/or lactones is present, preferably in a total amount of 0.1 to 2 wt. %, particularly preferably in a total amount of 0.6 to 1.5 wt. %, exceptionally preferably in a total amount of 0.8 to 1.1 wt. %, in each case based on the weight of free glucoheptonic acid in relation to the weight of the alkalizing component.

Glucoheptonic acid (226.18 g/mol) is also known as d-glycero-d-gulo heptonic acid. Physiologically acceptable salts of glucoheptonic acid suitable in the context of the present disclosure include in particular the salts of alkali metals, alkaline earth metals and earth metals, in particular of lithium, sodium, potassium, magnesium and calcium, particularly preferably sodium and potassium, exceptionally preferably sodium. Sodium glucoheptonate (INCI: sodium gluceptate; 248 g/mol), which is extremely preferred as contemplated herein, is commercially available.

Lactones of glucoheptonic acid preferred as contemplated herein include the 1,4-lactone (melting point 151° C.) and the 1,5-lactone, with the 1,4-lactone being exceptionally preferred.

Alkalizing components preferred as contemplated herein are exemplified in that glucoheptonic acid and/or at least one of its physiologically compatible salts and/or lactones is/are present in a total amount of 0.1 to 2 wt. %, particularly preferably in a total amount of 0.6 to 1.5 wt. %, exceptionally preferably in a total amount of 0.8 to 1.1 wt. %, the amounts being based on the weight of free glucoheptonic acid in relation to the weight of the alkalizing component as contemplated herein.

Surprisingly, it was found that the hair conditioning properties of a bleaching agent based on an alkalizing component preferred as contemplated herein could be further improved by the addition of at least one aminated silicone.

In another preferred embodiment of the present disclosure, the alkalizing component as contemplated herein comprises at least one aminated silicone. Preferred aminated silicones are selected from compounds of structural formula (I), (I)

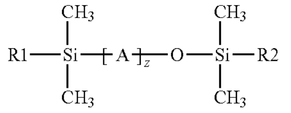

with

A =

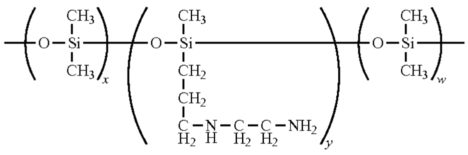

wherein i. x and y stand independently for numbers from 1 to 100, ii. w stands for a number from 0 to 100, iii. z is a number from 1 to 100, whereby, if z≥is 2, the respective values x, y and w in a structural element A can each be selected independently of preceding structural elements A and iv. R1 and R2 independently of one another represent a linear or branched, saturated, unsaturated or polyunsaturated $C_5$-$C_{20}$ alkyl group, a hydroxy group, a $C_1$-$C_{30}$ alkoxy group, a carboxy-$C_1$-$C_{30}$ alkyl group or a $C_1$-$C_6$ alkyl-(O—$CH_2$—$CH_2$)n-O— group, wherein n is an integer from 1 to 60.

The structural elements A of the compound of the formula (I) are each composed of one or more elements 3-[(2-aminoethyl)amino]propyl-methyl-siloxane and one or more elements dimethylsiloxane. The number of dimethylsiloxane elements is defined by the parameter x. The number of 3-[(2-aminoethyl)amino]propyl-methyl-siloxane elements is defined by the parameter y. As contemplated herein, the values of the parameters x and y stand independently of each other for numbers between 1 and 100.

The number of structural elements A is defined by the parameter z. As contemplated herein, the value of the parameter z is between 1 and 100. If z≥2, the parameters x and y can be selected in each structural element A independently of preceding structural elements A. It follows that for case z≥2, the individual structural elements A may differ from one another in their number of 3-[(2-aminoethy)amino] propyl-methyl-siloxane elements and/or in their number of dimethylsiloxane elements.

The siloxane backbone of the compound(s) of formula (I) is terminated at both ends by the radicals R1 and R2, where R1 and R2, independently of one another, may represent a linear or branched, saturated, unsaturated or polyunsaturated $C_5$-$C_{20}$ alkyl chain, a hydroxyl group, a $C_1$-$C_{30}$ alkoxy group or a $C_1$-$C_6$ alkyl-(O—$CH_2$—$CH_2$)$_n$—O— group.

Another alkalizing component which is particularly preferred as contemplated herein comprises, by weight, at least one aminated silicone selected from compounds of the structural formula (I) in a total amount of 0.1 to 2 wt. %, particularly preferably in a total amount of 0.7 to 1.5 wt. %, exceptionally preferably in a total amount of 0.9 to 1.1 wt. %.

If R1 and/or R2 stand for a branched, saturated, unsaturated or polyunsaturated $C_5$-$C_{20}$ alkyl radical, the siloxane skeleton is terminated with a fatty alkyl chain. Fatty alkyl chains in the sense of the present disclosure are all linear and/or branched, saturated and/or unsaturated and/or polyunsaturated carbon chains whose carbon chain is preferably a $C_6$-$C_{30}$ chain, particularly preferably a $C_8$-$C_{24}$ chain and particularly a $C_{14}$-$C_{20}$ chain. Examples of fatty alkyl chains as contemplated herein are hexyl, heptyl, octyl, nonyl, decyl, dodecyl, tetradecyl, pentadecyl, hexadecyl, heptadecyl, octadecyl, nonadecyl, eicosyl, docosyl, tetracosyl, hexacosyl, iso-stearyl, (9Z)-tetradeca-9-enyl, (9Z)-hexadeca-9-enyl, (6Z)-Octadeca-6-enyl, (9Z)-Octadeca-9-enyl, (9E)-Octadeca-9-enyl, (11E)-Octadeca-11-enyl, (9Z)-Eicosa-9-enyl, (11Z)-Eicosa-11-enyl, (11Z)-Docosa-11-enyl, (13Z)-Docosa-13-enyl, (15Z)-Tetracosa-15-enyl, (9Z,12Z)-Octadeca-9,12-dienyl, (9Z,12Z,15Z)-Octadeca-9,12,15-trienyl, (6Z,9Z,12Z)-Octadeca-6,9,12-trienyl, (8E,10E,12Z)-Octadeca-8,10,12-trienyl, (9Z,11E,13Z)-Octadeca-9,11,13-trienyl, (9Z,11E,13E)-Octadeca-9,11,13-trienyl, (9E,11E,13E)-Octadeca-9,11,13-trienyl, (5Z,8Z,11Z,14Z)-Eicosa-5,8,11,14-tetraenyl, (5Z,8Z,11Z,14Z,17Z)-Eicosa-5,8,11,14 17-pentaenyl, (7Z,10Z,13Z,16Z,19Z)-Docosa-7,10,13,16,19-pentaenyl, (4Z,7Z,10Z,13Z,16Z,19Z)-Docosa-4,7,10,13,16,19-hexaenyl. In a preferred embodiment of the present disclosure, the radicals $R^1$ and $R^2$ independently of one another represent linear alkyl chains, preferably $C_{14}$-$C_{20}$alkyl, particularly preferably tetradecyl, pentadecyl, hexadecyl, heptadecyl, octadecyl, nonadecyl or eicosyl. Particularly preferred residues $R^1$ and/or $R^2$ are hexadecyl (cetyl) and/or octadecyl (stearyl). Cetearyl is a mixture of cetyl and stearyl; this mixture is also preferred.

In a preferred embodiment, the alkalizing component as contemplated herein comprises a compound of the formula (I) in which the substituents $R^1$ and $R^2$ independently of one another represent a linear or branched, saturated, unsaturated or polyunsaturated $C_5$-$C_{20}$-alkyl chain, preferably a linear $C_{14}$-$C_{20}$-alkyl chain, in particular preferably a member of the group $H_3C-(CH_2)_{13}-$, $H_3C-(CH_2)_{15}-$, $H_3C-(CH_2)_{17}-$, $H_3C-(CH_2)_{19}-$.

As contemplated herein, compounds of the formula (I) in which the radicals $R_1$ and $R_2$ independently of one another represent $H_3C-(CH_2)_{15}-$ or $H_3C-(CH_2)_{17}-$ are particularly preferred. In this case, the invented amodimethicone is a bis-tearyl amodimethicone.

In a further preferred embodiment, the alkalizing component as contemplated herein comprises at least one compound of the formula (I) in which $R^1$ is $H_3C-(CH_2)_{15}-$ or $H_3C-(CH_2)_{17}-$ and $R_2$ is $H_3C-(CH_2)_{15}-$ or $H_3C-(CH_2)_{17}-$. Such compounds are known under the INCI designation Bis-Cetearyl Amodimethicone, which is commercially available for example under the trade name Silsoft AX from the company Momentive. Accordingly, a further alkalizing component particularly preferred as contemplated herein is exemplified in that it contains, by weight, bis-cearyl amodimethicone in a total amount of 0.1 to 2 wt. %, particularly preferably in a total amount of 0.7 to 1.5 wt. %, exceptionally preferably in a total amount of 0.9 to 1.1 wt. %.

Accordingly, a particularly preferred alkalizing component as contemplated herein comprises at least one compound of the formula (Ia), (Ib) and/or (Ic), to 2 wt. %, particularly preferably in a total amount of from 0.7 to 1.5 wt. %, exceptionally preferably in a total amount of from 0.9 to 1.1 wt. %.

A further aminated silicone preferred as contemplated herein is selected from at least one compound of structural formula (II), (II)

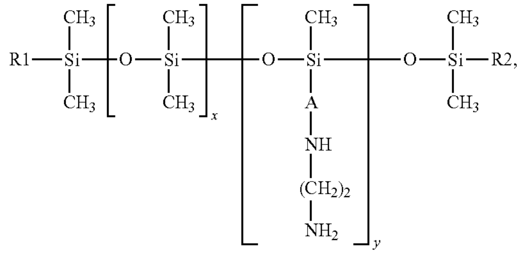

wherein i. x and y independently of one another stand for numbers from 1 to 5000, where x preferably stands for numbers (Ia)

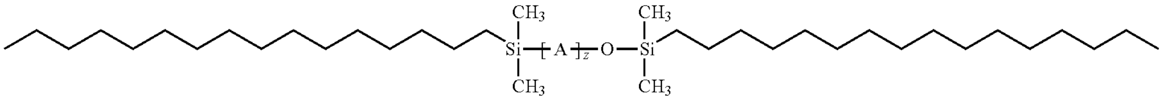

(Ib)

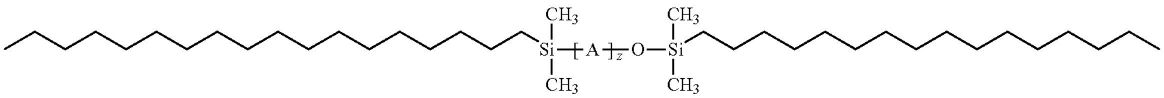

(Ic)

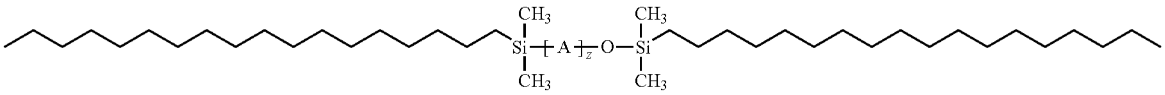

where the structural unit (A) in the formulae (Ia), (Ib), (Ic) each independently of one another is

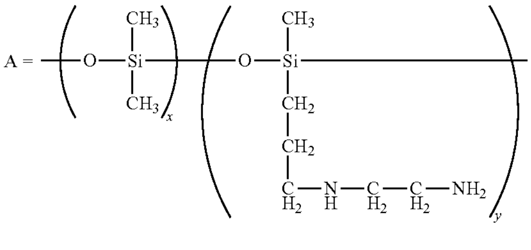

wherein x and y independently of each other stand for values between 1 and 100, z stands for values between 1 and 100, whereby, if z is 2, the respective values x and y in a structural element A can each be selected independently of preceding structural elements A.

Another particularly preferred alkalizing component comprises, in each case by weight, at least one compound of the formula (Ia), (Ib) and/or (Ic) in a total amount of from 0.1 from 10 to 1800 and particularly preferably 100 to 1000, where y preferably stands for numbers from 1 to 80, ii. R1 and R2 independently represent a methyl group or a hydroxy group, and iii. A represents a linear or branched alkylene group with 2 to 8, preferably 3-6 and particularly preferably 3 or 4 carbon atoms, preferably a linear propylene group $-CH_2-CH_2-CH_2-$ or a branched isobutylene group $-CH_2-CH(CH_3)-CH_2$.

A further alkalizing component particularly preferred as contemplated herein comprises, in each case based on its weight, at least one aminated silicone of the structural formula (II) in a total amount of 0.1 to 2 wt. %, particularly preferably in a total amount of 0.7 to 1.5 wt. %, exceptionally preferably in a total amount of 0.9 to 1.1 wt. %.

Another aminated silicone preferred by the present disclosure is selected from at least one linear copolymer comprising blocks of polydimethylsiloxane units and blocks of polyethylene glycol bis(2-methyl-2-propen-1-yl)ether monomers having the following structure (III)

(III)

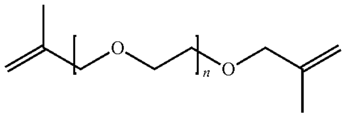

where n=14 and which is terminated with 3-{3-[bis(2-hydroxypropyl)amino]-2-hydroxypropoxy]propyl groups. A preferred linear copolymer of this type has the INCI designation Bis-Diisopropanolamino-PG-Propyl-Dimethicone/Bis-Isobutyl PEG-14 Copolymer. This linear copolymer is available in emulsified form under the trade name DC CE-8411 Smooth Plus Emulsion from Dow Corning.

Alkalizing components preferred as contemplated herein comprise at least one aminated silicone selected from compounds of the structural formula (I), compounds of the structural formula (II), linear copolymers comprising blocks of polydimethylsiloxane units and blocks of polyethylene glycol-bis(2-methyl-2-propen-1-yl)ether monomers of the following structure (III)

(III)

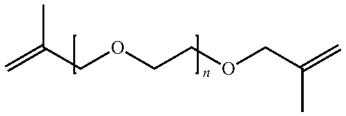

where n=14 and which are terminated with 3-{3-[bis(2-hydroxypropyl)amino]-2-hydroxypropoxy]propyl groups, and mixtures of these compounds.

Other alkalizing components preferred as contemplated herein comprise at least one aminated silicone selected from compounds of the structural formula (I), compounds of the structural formula (II), linear copolymers comprising blocks of polydimethylsiloxane units and blocks of polyethylene glycol-bis(2-methyl-2-propen-1-yl)ether monomers of the following structure (III)

(III)

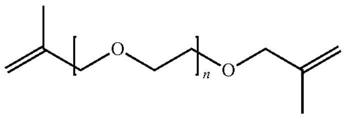

with n=14 and which are terminated with 3-{3-[bis(2-hydroxypropyl)amino]-2-hydroxypropoxy]propyl groups, and mixtures of these compounds, in a total amount of 0.1-2 wt. %, preferably 0.7-1.5 wt. %, particularly preferably 0.9 to 1.1 wt. %, in each case based on the weight of the alkalizing component.

Alkalizing components preferred as contemplated herein are exemplified by the fact that they do not contain 1,2-propylene glycol. During the development work on the present disclosure, it was found that 1,2-propylene glycol can negatively affect the skin compatibility of the whitening agent.

Optional Blonde Booster

Optionally, an anhydrous persulfate-comprising composition can be added to the mixture of alkalizing component and aqueous hydrogen peroxide preparation as contemplated herein or preferred as contemplated herein, which further enhances the lightening and bleaching performance of the entire bleaching composition. The anhydrous persulfate percarbonate comprising composition is often also called bleach booster or blonde booster. The blond booster preferred by the present disclosure is in powder form.

As contemplated herein, the term "powder" or "powdery" means a solid, free-flowing dosage form comprising individual particles that are solid at 20° C. and 1013 mbar, in which the particles have particle sizes ranging from 0.1 μm to a maximum of 1.6 mm. The determination of particle sizes can preferably be done by laser diffraction measurement according to ISO 13320-1 (2009). If necessary, the particle size of the blonde booster can be adjusted by physical treatment, such as sieving, pressing, granulating or pelletizing, or by the addition of certain auxiliary substances, to meet the requirements of the blonde booster, for example to allow better miscibility of the individual powder constituents or miscibility of the blonde booster with the agent of or preferred present disclosure and an aqueous hydrogen peroxide preparation.

Blond boosters preferably used as contemplated herein have a bulk density in the range of 500 to 1000 g/l (grams/liter), preferably 550 to 900 g/l, particularly preferably 600 to 820 g/l. The determination of the bulk density is preferably carried out according to EN ISO 600 DIN 53468.

Unless otherwise stated, all temperature specifications refer to a pressure of 1013 mbar.

The blond booster preferably used as contemplated herein comprises, as a first essential component, at least one oxidizing agent selected from inorganic salts of a peroxosulfuric acid.

The blond boosters are percarbonate-free, especially free of sodium percarbonates. Sodium percarbonates are sodium carbonate-hydrogen peroxide complexes. Commercial sodium percarbonate has the average composition 2 $Na_2CO_3 \cdot 3\ H_2O_2$. Sodium percarbonate is present as a white, water-soluble powder that easily breaks down into sodium carbonate and "active" oxygen that has a bleaching and oxidizing effect.

Peroxosulfuric acids are peroxodisulphuric acid and peroxomonosulfuric acid (Caro's acid).

Preferably at least one inorganic salt of peroxosulfuric acid selected from ammonium peroxodisulfate, alkali metal peroxodisulfates, ammonium peroxomonosulfate, alkali metal peroxomonosulfates and alkali metal hydrogen peroxomonosulfates. Ammonium peroxodisulfate, potassium peroxodisulfate, sodium peroxodisulfate and potassium hydrogen peroxomonosulfate are particularly preferred. Furthermore, during the work on the present disclosure, it has proved to be particularly preferred if the blonde booster preferably used as contemplated herein comprises at least two different peroxodisulfates. Preferred peroxodisulfate salts are combinations of ammonium peroxodisulfate and potassium peroxodisulfate and/or sodium peroxodisulfate.

Blond boosters preferably used as contemplated herein contain at least one oxidizing agent selected from inorganic salts of a peroxosulfuric acid in a total amount of 5-100 wt. %, preferably 10-98 wt. %, particularly preferably 25-70 wt. %, exceptionally preferably 30-50 wt. %, in each case based on the weight of the blond booster.

The water-free blonde boosters preferably used as contemplated herein have a water content of 0 to 8% by weight, preferably 0.1 to 5% by weight, particularly preferably 0.5 to 2.5% by weight, of water, in each case based on the weight of the blonde booster. With the above mentioned water contents ranging from 0 to 8% by weight, blonde boosters are, by definition, regarded as anhydrous for the purposes of the present application. These figures refer to the content of free water. Not taken into account is the content of molecularly bound water or water of crystallization, which individual powder components may have.

The water content can be determined by Karl Fischer titration according to ISO 4317 (Version 2011-12).

Blond boosters preferably used as contemplated herein preferably additionally contain at least one inorganic alkalizing agent which is solid at 20° C. and 1013 mbar and which is preferably included in a total amount of 1-60% by weight, preferably 5-55% by weight, particularly preferably 10-50% by weight, extremely preferably 15-45% by weight, in each case based on the weight of the blond booster. As contemplated herein, particularly preferred inorganic alkalizing agents which are solid at 20° C. and 1013 mbar are selected from alkali metal silicates, alkaline earth metal silicates, alkaline earth metal hydroxide carbonates, alkaline earth metal carbonates, alkali metal hydroxides, alkaline earth metal hydroxides, (earth) alkali metal phosphates and (earth) alkali metal hydrogen phosphates and mixtures of these substances. As contemplated herein, particularly preferred inorganic alkalizing agents which are solid at 20° C. and 1013 mbar are selected from sodium silicates with a molar $SiO_2/Na_2O$ ratio of 2, preferably from 2.5 to 3.5, and from magnesium hydroxide carbonates and mixtures of these substances. As contemplated herein, preferred magnesium hydroxide carbonates are those with the formula $MgCO_3 \cdot Mg(OH)_2 \cdot 2\ H_2O$ and those with the formula $MgCO_3 \cdot Mg(OH)_2$. Magnesium hydroxide carbonate with the formula $MgCO_3 \cdot Mg(OH)_2$ is particularly preferred as contemplated herein.

Blond boosters which are used with particular preference as contemplated herein contain, in each case based on their total weight, 20-50% by weight, preferably 22-40% by weight, particularly preferably 23-30% by weight of sodium silicates with a molar $SiO_2/Na_2O$ ratio of ≥2, preferably from 2.5 to 3.5, as alkalizing agents solid at 20° C. and 1013 mbar.

Further blond boosters preferably used as contemplated herein contain, based on their total weight, 20-50% by weight, preferably 30-45% by weight, particularly preferably 34-40% by weight of sodium silicates with a molar $SiO_2/Na_2O$ ratio of ≥2, preferably from 2.5 to 3.5, and 2 to 20% by weight, preferably 5 to 15% by weight, particularly preferably 10 to 13% by weight of magnesium hydroxide carbonate with the formula $MgCO_3 \cdot Mg(OH)_2$ as an inorganic alkalizing agent which is solid at 20° C. and 1013 mbar.

Blond boosters used as contemplated herein do not contain any polymer or copolymer with acrylate-, methacrylate- or vinyl-comprising monomers and no polyurethane.

Another object of the present disclosure is a packaging unit (kit-of-parts) comprising—packaged separately from each other—.

at least one container (C1) comprising an alkalizing component (M1) as contemplated herein or preferred as contemplated herein, and at least one container (C2) comprising an oxidant preparation (M2) which comprises 40-96 wt. %, preferably 68-93 wt. %, particularly preferably 72-85 wt. %, of water, further hydrogen peroxide in a total amount of 0.5 to 23 wt. %, further preferably 2.5 to 21 wt. %, particularly preferably 4 to 20 wt.-%, very particularly preferably 5 to 18 wt. % and exceptionally preferably 6 to 12 wt. %, and has a pH value in the range of 2.0 to 6.5, preferably 2.5-5.5, particularly preferably 2.8 to 5.0, in each case measured at 20° C., wherein the wt. % data for (M2) relate in each case to the weight of the oxidant preparation (M2), and the oxidant preparation (M2) not comprising a polymer or copolymer with acrylate-, methacrylate- or vinyl-comprising monomers and not comprising a polyurethane.

As contemplated herein, preferred two-part blonding kits comprising the above-mentioned components (M1) and (M2) are composed with respect to the weight ratio (M1):(M2) of the two components to one another such that the weight ratio (M1):(M2) is in the range from 1:0.8 to 1:2.5, preferably 1:1 to 1:2.

What has been said above and below for the preferred embodiments of the agent (M1) as contemplated herein and the agent (M2) used as contemplated herein applies mutatis mutandis to the blonding kits as contemplated herein and preferred as contemplated herein.

Another object of the present disclosure is a packaging unit (kit-of-parts) comprising—packaged separately from each other—.

at least one container (C1) comprising an alkalizing component (M1) as contemplated herein or preferred as contemplated herein, and at least one container (C2) comprising an oxidant preparation (M2) which comprises 40-96 wt. %, preferably 68-93 wt. %, particularly preferably 72-85 wt. %, of water, further hydrogen peroxide in a total amount of 0.5 to 23 wt. %, further preferably 2.5 to 21 wt. %, particularly preferably 4 to 20 wt.-%, very particularly preferably 5 to 18 wt. % and exceptionally preferably 6 to 12 wt. %, and has a pH value in the range of 2.0 to 6.5, preferably 2.5-5.5, particularly preferably 2.8 to 5.0, in each case measured at 20° C., wherein the wt. % data for (M2) relate in each case to the weight of the oxidant preparation (M2), and the oxidant preparation (M2) not comprising a polymer or copolymer with acrylate-, methacrylate- or vinyl-comprising monomers and not comprising a polyurethane, and at least one container (C3) comprising a preferably powdered blonde booster composition (M3) which is free from percarbonates, polymers and copolymers with acrylate, methacrylate or vinyl-comprising monomers and is free from polyurethanes and the at least one oxidizing agent, which is selected from inorganic salts of a peroxosulfuric acid and mixtures thereof, in a total amount of 5-100% by weight, preferably 10-98% by weight, particularly preferably 25-70% by weight, extremely preferably 30-50% by weight %, in each case based on the weight of the blonde booster, and from 0 to 8% by weight, preferably 0.1 to 5% by weight, particularly preferably 0.5 to 2.5% by weight, water, in each case based on the weight of the blond booster.

As contemplated herein, preferred three-part blonding kits comprising the above-mentioned components (M1), (M2) and (M3) are composed with respect to the weight ratio (M1):(M2):(M3) of the three components to each other in such a way that the weight ratio (M1):(M2) is in the range of 1:0.8 to 1:2.5, preferably 1:1 to 1:2, and (M3) is present in an amount of 5-25 wt.-%. %, preferably 7-20 wt. %, particularly preferably 7.5-17 wt. %, based on the weight of the total mixture of (M1), (M2) and (M3).

What has been said above and below for the preferred embodiments of (M1) (M2) and (M3) applies mutatis mutandis to the Preferred Blonding Kits.

A further subject of the present disclosure is a process for oxidative hair lightening or bleaching which comprises the following process steps:

i) providing an alkalizing component (M1) as contemplated herein or preferred as contemplated herein, and ii) Providing an oxidant preparation (M2) comprising 40-96 wt. %, preferably 68-93 wt. %, particularly preferably 72-85 wt. %, of water, further comprising hydrogen peroxide in a total amount of 0.5 to 23 wt. %, further preferably 2.5 to 21 wt. %, particularly preferably 4 to 20 wt. %, most preferably 5 to 18 wt. % and exceptionally preferably 6 to 12 wt.-%, and having a pH in the range from 2.0 to 6.5, preferably 2.5-5.5, particularly preferably 2.8 to 5.0, in each case measured at 20° C., the wt. % data in each case being based on the weight of the oxidant preparation (M2), the oxidant preparation (M2) comprising no polymer or copolymer with acrylate-, methacrylate- or vinyl-comprising monomers and no polyurethane, iii) Mixing the alkalizing component (M1) with the oxidizing agent preparation (M2), preferably in a weight ratio (M1):(M2) in the range of 1:0.8 to 1:2.5, preferably 1:1 to 1:2, directly followed by iv) Apply the mixture obtained in step iii) to the hair and leave this mixture on the hair for a time of 1 to 60 minutes, preferably of 20 to 45 minutes, at room temperature and/or at 30-60° C., preferably at 32-50° C., v) rinsing the hair with water and/or a cleansing composition, and vi) if necessary, apply an after-treatment agent to the hair and rinse if necessary, followed by drying.

A further subject of the present disclosure is a process for oxidative hair lightening or bleaching which comprises the following process steps:

i) providing an alkalizing component (M1) as contemplated herein or preferred as contemplated herein, and ii) Providing an oxidant preparation (M2) comprising 40-96 wt. %, preferably 68-93 wt. %, particularly preferably 72-85 wt. %, of water, further comprising hydrogen peroxide in a total amount of 0.5 to 23 wt. %, further preferably 2.5 to 21 wt. %, particularly preferably 4 to 20 wt. %, most preferably 5 to 18 wt. % and exceptionally preferably 6 to 12 wt.-%, and having a pH in the range from 2.0 to 6.5, preferably 2.5-5.5, particularly preferably 2.8 to 5.0, in each case measured at 20° C., the wt. % data in each case being based on the weight of the oxidizer preparation (M2), the oxidizer preparation (M2) comprising no polymer or copolymer with acrylate-, methacrylate- or vinyl-comprising monomers and no polyurethane, iii) Providing a blond booster composition (M3), preferably in powder form, which is free from percarbonates, polymers and copolymers with acrylate-, methacrylate- or vinyl-comprising monomers and is free from polyurethanes and which comprises at least one oxidizing agent selected from inorganic salts of a peroxosulfuric acid as well as mixtures thereof, in a total amount of 5-100 wt.-%, preferably 10-98 wt.-%, particularly preferably 25-70 wt.-%, extremely preferably 30-50 wt.-%, each based on the weight of the blond booster. %, preferably 10-98 wt. %, particularly preferably 25-70 wt. %, exceptionally preferably 30-50 wt. %, in each case based on the weight of the blond booster, and from 0 to 8 wt. %, preferably 0.1 to 5 wt. %, particularly preferably 0.5 to 2.5 wt. %, of water, in each case based on the weight of the blond booster, iv) Mixing the alkalizing component (M1) with the oxidizing agent preparation (M2) and with the blonde booster composition (M3), preferably in such a weight ratio (M1):(M2):(M3) that the weight ratio (M1):(M2) is in range from 1:0.8 to 1:2.5, preferably 1:1 to 1:2, and (M3) in an amount of 5-25 wt. %, preferably 7-20 wt. %, especially preferably 7.5-17 wt. %, based on the weight of the entire mixture of (M1), (M2) and (M3), is included, directly afterwards v) Apply the mixture obtained in step iv) to the hair and leave this mixture on the hair for a time of 1 to 60 minutes, preferably of 20 to 45 minutes, at room temperature and/or at 30-60° C., preferably at 32-50° C., vi) rinsing the hair with water and/or a cleansing composition, and vii) if necessary, apply an after-treatment agent to the hair and rinse if necessary, followed by drying.

Processes preferred as contemplated herein for oxidative hair lightening or bleaching using the aforementioned components (M1), (M2) and (M3) are designed with respect to the weight ratio (M1):(M2):(M3) of the three components to one another in such a way that the weight ratio (M1):(M2) is in the range from 1:0.8 to 1:2.5, preferably 1:1 to 1:2, and (M3) is present in an amount of 5-25 wt. % of the total weight of the three components. %, preferably 7-20 wt. %, particularly preferably 7.5-17 wt. %, based on the weight of the total mixture of (M1), (M2) and (M3).

What has been said above and below for the preferred embodiments of the alkalizing component (M1) as contemplated herein and the agents (M2) and (M3) used as contemplated herein applies mutatis mutandis to the processes for oxidative hair lightening or bleaching as contemplated herein and preferred as contemplated herein.

For oxidative hair lightening processes, the alkalizing component (M1) as contemplated herein is usually mixed with an aqueous oxidizing agent-comprising composition (M2) to form the ready-to-use hair lightening or bleaching agent immediately before application to the hair, and then applied to the hair. In most cases, the alkalizing component (M1) as contemplated herein and the oxidizing agent-comprising composition (M2) are matched to each other in such a way that, at a mixing ratio of 1 to 1, based on parts by weight, there is an initial concentration of hydrogen peroxide of 0.5-12 wt. %, preferably 2-10 wt. %, particularly preferably 3-6 wt. % hydrogen peroxide (calculated as 100% H2O2), in each case based on the weight of the application mixture, in the finished application mixture. However, it is just as well possible to match the alkalizing component (M1) as contemplated herein and the oxidizing agent-comprising composition (M2) to each other in such a way that the concentrations required in the ready-to-use lightening or bleaching agent (application mixture) are obtained by mixing ratios other than 1:1, for example by a weight-related mixing ratio of 1:2 or 1:3 or even 2:3.

As contemplated herein, preferred weight-related mixing ratios (M1):(M2) are in the range from 1:0.8 to 1:2.5, particularly preferred in the range from 1:1 to 1:2. As contemplated herein, the term “room temperature” refers to the temperature in the room in which a person usually uses a hair whitening or bleaching product, i.e. usually a bathroom or hairdressing salon, where the temperature is in the range 10-29° C.

Leaving the hair lightening application mixture in process step v) in the hair lightening or bleaching processes as contemplated herein or preferred as contemplated herein can also take place at minimum 30° C., preferably at 30-60° C., particularly preferably at 32-50° C., if the hair is heated, for example, with a heat hood or a radiant heater.

The oxidizing agent preparation (M2) used in lightening or bleaching kits as contemplated herein and in lightening or bleaching processes preferred as contemplated herein comprises, in each case based on its weight, 40-96 wt. %, preferably 68-93 wt. %, particularly preferably 72-85 wt. %, of water.

The oxidizing agent preparation (M2) used in whitening or bleaching kits as contemplated herein and preferred as contemplated herein as well as in hair whitening or bleaching processes as contemplated herein and preferred as contemplated herein further comprises, in each case based on its weight, 0.5-23% by weight, more preferably 2.5-21% by weight, particularly preferably 4-20% by weight, very particularly preferably 5-18% by weight and extremely preferably 6-12% by weight, of hydrogen peroxide.

To stabilize the hydrogen peroxide, the oxidizer preparation (M2) has a pH in the range from 2.0 to 6.5, preferably 2.5-5.5, particularly preferably 2.8 to 5.0, in each case measured at 20° C. The oxidant preparation (M2) does not contain any polymer or copolymer with acrylate-, methacrylate- or vinyl-comprising monomers and no polyurethane.

Ready-to-use hair lightening compositions which are preferred as contemplated herein and comprise an alkalizing component (M1) as contemplated herein or preferred as contemplated herein and an oxidizing agent preparation (M2) and optionally a blond booster (M3) have a viscosity in the range from 5,000 to 45,000 mPa-s, preferably 10,000 to 35,000 mPa-s, particularly preferably 15,000 to 30,000 mPa-s, in each case measured at 20° C. These viscosities are excellent for the handling of this agent itself (preparation, spread ability on the hair, residence behavior during the application time). The parameters for the viscosity measurements are:

Device: Brookfield viscometer RDV-II+; temperature: 20° C.; spindle 5; shear rate: 4 revolutions per minute (4 RPM).

The oxidizing agent preparation (M2) used in hair lightening kits preferred as contemplated herein and in hair lightening processes preferred as contemplated herein comprises at least one surfactant selected from anionic surfactants and non-ionic surfactants and mixtures thereof in a total amount of 0.05-2 wt. %, preferably 0.3-1.5 wt.-%, and at least one linear saturated 1-alkanol having 14 to 22 carbon atoms selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of 1-5 wt. %, preferably 1.5-4 wt. %, all amounts being based on the weight of the oxidant preparation (M2).

For the purposes of the present application, the aforementioned linear, saturated 1-alkanols with a hydroxyl group are not counted as surfactants.

The anionic surfactants used in the oxidizing agent preparations (M2) used as contemplated herein are selected from the same anionic surfactants from which the anionic surfactants included in the agents (M1) used as contemplated herein are selected.

Particularly preferred non-ionic surfactants for the oxidant preparations (M2) used as contemplated herein are selected from castor oil ethoxylated with 7-80 mol ethylene oxide per mol, ethoxylated $C_5$-$C_{24}$ alkanols with 5-30 mol ethylene oxide per mol, ethoxylated $C_8$-$C_{24}$ carboxylic acids with 5-30 mol ethylene oxide per mol, sorbitan monoesters of linear saturated and unsaturated $C_{12}$-$C_{30}$ carboxylic acids which may be hydroxylated, in particular those of myristic acid, palmitic acid, stearic acid or of mixtures of these fatty acids, alkyl mono- and oligoglycosides comprising 8 to 22 carbon atoms in the alkyl radical and their ethoxylated analogues, and mixtures of the abovementioned substances, ethoxylated with 4-50 mol ethylene oxide per mol.

The ethoxylated $C_8$-$C_{24}$-Alkanols have the formula $R^1O(CH_2CH_2O)_nH$, where $R^1$ stands for a linear or branched alkyl and/or alkenyl radical with 8-24 carbon atoms and n, the average number of ethylene oxide units per molecule, for numbers from 5-30, preferably 6-20, particularly preferably 6 to 12 moles of ethylene oxide to 1 mole of alkanol, which is preferably selected from caprylic alcohol, 2-Ethylhexyl alcohol, capric alcohol, lauryl alcohol, isotridecyl alcohol, tridecyl alcohol, myristyl alcohol, cetyl alcohol, palmitoleyl alcohol, stearyl alcohol, isost, Oleyl alcohol, elaidyl alcohol, petroselinyl alcohol, arachyl alcohol, gadoleyl alcohol, behenyl alcohol, erucyl alcohol and brassidyl alcohol and from their technical mixtures. Adducts of 10-100 moles of ethylene oxide to technical fatty alcohols with 12-18 carbon atoms, such as coconut, palm, palm kernel or tallow fatty alcohols, are also suitable. Particularly preferred are trideceth-6, isotrideceth-6, undeceth-6, myreth-6, laureth-10, laureth-12, laureth-15, laureth-20, laureth-30, myreth-10, myreth-12, myreth-15, myreth-20, myreth-30, ceteth-10, ceteth-12, ceteth-15, ceteth-20, ceteth-30, steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, and Coceth-10, Coceth-12, Coceth-15, Coceth-20 and Coceth-30; exceptionally preferred are castor oil ethoxylates, in particular PEG-40 castor oil, and ethoxylated fatty alcohols, in particular Ceteth-20 and Steareth-20, as well as mixtures of castor oil ethoxylates and ethoxylated fatty alcohols, in particular mixtures of PEG-40 castor oil, Ceteth-20 and Steareth-20.

Oxidant preparations (M2) preferred as contemplated herein contain at least one anionic surfactant in a total amount of 0.5-2.5 wt. %, preferably 1.0 to 1.6 wt. %, in each case based on the weight of (M2). Oxidant preparations (M2) preferred as contemplated herein contain at least one non-ionic surfactant selected from castor oil ethoxylates, in particular PEG-40 castor oil, and ethoxylated fatty alcohols, in particular ceteth-20 and steareth-20, and mixtures thereof, in a total amount of 0.5-2.5 wt. %, preferably 1.0 to 1.6 wt. %, in each case based on the weight of (M2).

In a further preferred embodiment of the present disclosure, the oxidant preparation (M2) used as contemplated herein comprises at least one oil in a total amount of 0.2-50 wt. %, preferably 2-40 wt. %, particularly preferably 5-30 wt. %, exceptionally preferably from 10-12 wt. %, in each case based on the weight of the oxidant preparation (M2).

The at least one oil included in the oxidant preparation (M2) in a total amount of 0.2-50 wt. %, preferably 2-40 wt. %, particularly preferably 5-30 wt. %, exceptionally preferably 10-12 wt. %, in each case based on the weight of the preparation (M2), is preferably selected from natural and synthetic hydrocarbons, particularly preferably from mineral oil, kerosene oils, $C_{18}$-$C_{30}$ isoparaffins, especially isoeicosane, polyisobutenes and polydecenes, $C_8$-$C_{16}$ isoparaffins, and 1,3-di-(2-ethylhexyl)-cyclohexane; the benzoic acid esters of linear or branched $C_{8-22}$ alkanols; triglycerides of linear or branched, saturated or unsaturated, optionally hydroxylated $C_{8-30}$ fatty acids, in particular natural oils; the dicarboxylic acid esters of linear or branched $C_2$-$C_{10}$ alkanols; the esters of linear or branched saturated or unsaturated fatty alcohols with 2-30 carbon atoms with linear or branched saturated or unsaturated fatty acids with 2-30 carbon atoms, which may be hydroxylated; branched fatty alcohols; the $C_8$-$C_{22}$ fatty alcohol esters of monovalent or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols, and mixtures of the above mentioned substances. In this context, particularly preferred oils as contemplated herein are selected from at least one ester of linear or branched saturated or unsaturated fatty alcohols having 2-30 carbon atoms with linear or branched saturated or unsaturated fatty acids having 2-30 carbon atoms, which may be hydroxylated, and mixtures thereof; exceptionally preferably selected from isopropyl palmitate and isopropyl myristate and mixtures thereof.

Cationic Surfactant in the Oxidant Preparation (M2)

The above viscosity of agents (M1) preferred as contemplated herein is excellent for handling this agent itself (preparation, filling, dosing to prepare the mixture with the oxidant preparation). The oxidant preparation (M2) usually has a low viscosity in the range of 10-6000 mPas, preferably 200-5000 mPas, especially preferably 1000-4500 mPas, each measured at 20° C. For application to the hair, however, the application mixture should have a significantly higher viscosity so that it remains on the hair during the entire application time (in the range of 5-60 minutes, preferably 30-45 minutes) and does not drip down. A distinction is made here as to whether the application mixture is produced by shaking both compositions (M1) and (M2) and, if applicable, (M3) in an application bottle, from which the application mixture is applied to the hair immediately after mixing using an application spout as a bottle attachment (bottle application), or whether the application mixture is prepared by stirring the two compositions (M1) and (M2) and, if applicable, (M3) in a bowl, from which the application mixture is applied to the hair with a brush immediately after mixing (brush application). The bottle application is particularly suitable for colorants that are sold in retail outlets with a recommendation for use by the consumer himself. Brush application is particularly suitable for colorants that are prepared in the hairdressing salon by the hairdresser and applied to the consumer's hair.

Surprisingly, it was found that an application mixture with a viscosity particularly suitable for brush application is obtained by mixing the agent (M1) according to or preferred present disclosure with an oxidizing agent preparation (M2) comprising at least one cationic surfactant. Upon mixing, the interaction between the at least one anion surfactant and the at least one cation surfactant results in the desired increase in viscosity. The resulting paste-like consistency of the application mixture leads to optimal application properties, especially for brush application.

In a further preferred embodiment of the present disclosure, the oxidant preparation (M2) used as contemplated herein comprises at least one cationic surfactant, preferably in a total amount of 0.05-3% by weight, particularly preferably of 0.1-1.5% by weight, extremely preferably of 0.3-0.9% by weight, in each case based on the weight of the oxidant preparation (M2).

Cationic surfactants are surfactants, i.e. surface-active compounds, each with one or more positive charges. Cationic surfactants contain only positive charges. Usually these surfactants are composed of a hydrophobic part and a hydrophilic head group, the hydrophobic part usually comprising a hydrocarbon backbone (e.g. comprising one or two linear or branched alkyl chains) and the positive charge(s) being located in the hydrophilic head group. Cationic surfactants adsorb at interfaces and aggregate in aqueous solution above the critical micelle formation concentration to form positively charged micelles.

As contemplated herein, cationic surfactants of the type of quaternary ammonium compounds, esterquats and alkylamidoamines are preferred. Preferred quaternary ammonium compounds are ammonium halides, such as alkyltrimethylammonium chlorides, dialkyldimethylammonium chlorides, trialkylmethylammonium chlorides, as well as the imidazolium compounds known under the INCI designations Quaternium-27 and Quaternium-83. Other preferred quaternary ammonium compounds are tetraalkylammonium salts, such as in particular the quaternium-52 known under the INCI designation, a poly(oxy-1,2-ethanediyl), ((octadecylnitrilio)tri-2,1-ethanediyOtris(hydroxy)phosphate (1:1) salt, which has the general structural formula (III), wherein x+y+z=10:

(III)

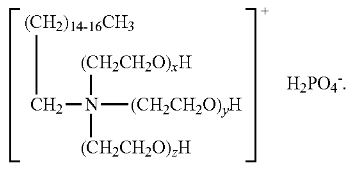

The long alkyl chains of the surfactants mentioned above preferably have 10 to 22, particularly preferably 12 to 18 carbon atoms. Behenyl trimethylammonium chloride, stearyl trimethylammonium chloride and cetyl trimethylammonium chloride are particularly preferred, with stearyl trimethylammonium chloride being extremely preferred. Further cationic surfactants suitable as contemplated herein are quaternized protein hydrolysates. Alkylamidoamines are usually produced by amidation of natural or synthetic fatty acids and fatty acid cuts with dialkylaminoamines. Tegoamid® S 18 (stearamidopropyldimethylamine) is a suitable compound from this group of substances. Esterquats are substances which contain both at least one ester function and at least one quaternary ammonium group as a structural element. Preferred esterquats are quaternized ester salts of fatty acids with triethanolamine, quaternized ester salts of fatty acids with diethanolalkylamines and quaternized ester salts of fatty acids with 1.2-dihydroxypropyl dialkylamines.

In terms of optimum application properties and optimal whitening results, C10-C22 alkyltrimethylammonium chlorides have proven to be particularly suitable. Particularly preferred oxidizing agent preparations (M2) used as contemplated herein are extremely preferred at least one cationic surfactant in a total amount of 0.05-3% by weight, particularly preferably 0.1-1.5% by weight from 0.3 to 0.9% by weight, based in each case on the weight of the oxidizing agent preparation (M2), preferably at least one surfactant selected from C10-C22-alkyltrimethylammonium chlorides, in particular selected from behenyltrimethylammonium chloride, stearyltrimethylammonium chloride and cetyltrimethylammonium chloride, and mixtures of these surfactants. Extremely preferred oxidant preparations (M2) used as contemplated herein contain stearyl trimethylammonium chloride in a total amount of 0.05-3 wt. %, particularly preferably 0.1-1.5 wt. %, extremely preferably 0.3-0.9 wt. %, each based on the weight of the oxidant preparation (M2).

A further packaging unit (kit-of-parts) preferred as contemplated herein and a further whitening process preferred as contemplated herein are the oxidant preparation (M2) comprises at least one cationic surfactant, preferably in a total amount of 0.05-3 wt. %, particularly preferably of 0.1-1.5 wt. %, exceptionally preferably of 0.3-0.9 wt. %, in each case based on the weight of the oxidant preparation (M2).

A further kit-of-parts preferred as contemplated herein and a further whitening process preferred as contemplated herein are each exemplified in that the oxidant preparation (M2) comprises at least one surfactant selected from anionic surfactants and non-ionic surfactants and mixtures thereof in a total amount of 0.05-2 wt. %, preferably 0.3-1.5 wt. %, and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of 1-5 wt. %, preferably 1.5-4 wt. %, in each case based on the weight of the oxidant preparation (M2).

A further kit-of-parts preferred as contemplated herein and a further whitening process preferred as contemplated herein are each exemplified in that the oxidant preparation (M2) comprises at least one surfactant selected from anionic surfactants and non-ionic surfactants and mixtures thereof in a total amount of 0.05-2 wt. %, preferably 0.3-1.5 wt. %, at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total amount of 1-5 wt.-%, preferably 1.5-1.5 wt.-%, preferably 1.5-1.5 wt.-%, and mixtures thereof %, preferably 1.5-4 wt. %, and at least one oil in a total amount of 0.2-50 wt. %, preferably 2-40 wt. %, particularly preferably 5-30 wt. %, exceptionally preferably 10-12 wt. %, in each case based on the weight of the oxidant preparation (M2).

The oxidizing agent preparations (M2) used as contemplated herein and preferably used as contemplated herein may also contain stabilizers, especially complexing agents, and pH buffer substances.

With respect to the cosmetic agent (M1) in container C1 and the oxidizing agent preparation (M2) in container C2 of the Preferred Kits, what has been said about the Preferred Cosmetics applies mutatis mutandis.

With regard to the cosmetic agent (M1) in container C1 of the processes for oxidative hair lightening as contemplated herein and preferred as contemplated herein, what has been said about the cosmetic agents as contemplated herein and preferred as contemplated herein applies mutatis mutandis.

With regard to the oxidant preparation (M2) in container C2 of the oxidative hair lightening processes as contemplated herein and preferred as contemplated herein, the same applies mutatis mutandis as to the oxidant preparations (M2) of the oxidative hair lightening kits as contemplated herein and preferred as contemplated herein.

The walls of containers C1 and C2 are preferably made of a polyolefin, such as polypropylene (PP), high density polyethylene (HDPE), medium density polyethylene (MDPE), low density polyethylene (LDPE), linear low density polyethylene (LLDPE). Among these, polyethylene, especially high density polyethylene (HDPE), is preferred.

For improved mixing of (M1) and (M2), it is preferred that the container (C2) comprising the oxidant preparation (M2) is designed as a bottle and has a reclosable opening, such as a snap-on or screw cap. This makes it easier to add the color-changing agent from container (C1), which in turn is preferably in the form of a polyolefin bottle.

The following examples are intended to illustrate the subject matter of the present disclosure, without restricting it thereto.

Experimental Part

The following alkalizing components (M1), oxidizer preparation (M2) and blond booster compositions (M3) were prepared by mixing the tabulated ingredients together (all amounts in wt. %):

TABLE 1

| Alkalizing component (M1) | |
|---|---|
| Xanthan gum | 1.500 |
| Cellulose Gum (Carboxymethylcellulose, Sodium Salt) | 0.900 |
| 2-Octyldodecanol | 4.520 |
| Ammonium hydroxide ($NH_4OH$) | 3.900 |
| Ammonium sulfate ($(NH_4)_2SO_4$) | 0.500 |
| Etidronic acid | 0.120 |
| Sodium laureth sulfate (2 EO) | 0.810 |
| Bis-Cetearyl Amodimethicone | 1.000 |
| Monoethanolamines (2-aminoethanol) | 2.000 |
| Sodium Gluceptate (Sodium Heptagluconate) | 1.050 |
| CI 77007 (ultramarine blue) | 0.098 |
| Kaolin | 0.010 |
| Perfume | 0.300 |
| Water, demineralized (Aqua) | 83.292 |
| | 100.000 |

Viscosity: 74,700 mPas (Brookfield viscometer RDV-II+; 20° C.; spindle 5; 4 RPM) pH value: 10.64 (20° C.)

TABLE 2

| Alkalizing component (M1) | |
|---|---|
| Xanthan gum | 1.500 |
| Cellulose Gum (Carboxymethylcellulose, Sodium Salt) | 0.900 |
| 2-Octyldodecanol | 4.520 |
| Etidronic acid | 0.120 |
| Sodium laureth sulfate (2 EO) | 0.810 |
| Bis-Cetearyl Amodimethicone | 1.000 |
| Monoethanolamine (2-aminoethanol) | 7.500 |
| Sodium Gluceptate (Sodium Heptagluconate) | 0.950 |
| CI 77007 (ultramarine blue) | 0.100 |
| Kaolin | 0.010 |
| Perfume | 0.200 |
| Water, demineralized (Aqua) | 82.390 |
| | 100.000 |

Viscosity: 80,400 mPas (Brookfield viscometer RDV-II+; 20° C.; spindle 5; 4 RPM) pH value: 11.24 (20° C.)

TABLE 3

| Alkalizing component (M1) | |
|---|---|
| Xanthan gum | 1.500 |
| Cellulose Gum (Carboxymethylcellulose, Sodium Salt) | 0.900 |
| 2-Octyldodecanol | 4.520 |
| Ammonium hydroxide ($NH_4OH$) | 3.900 |
| Ammonium sulfate ($(NH_4)_2SO_4$) | 0.500 |
| Etidronic acid | 0.120 |
| Sodium laureth sulfate (2 EO) | 0.810 |
| Bis-Cetearyl Amodimethicone | 1.000 |
| Sodium Gluceptate (Sodium Heptagluconate) | 1.050 |
| CI 77007 (ultramarine blue) | 0.100 |
| Perfume | 0.400 |
| Water, demineralized (Aqua) | 85.200 |
| | 100.000 |

Viscosity: 78,700 mPas (Brookfield viscometer RDV-II+; 20° C.; spindle 5; 4 RPM) pH value: 10.48 (20° C.)

TABLE 4

| Oxidizer preparation (M2) | |
|---|---|
| Hydrogen peroxide | 11.500 |
| Isopropyl myristate | 10.000 |
| Cetearyl alcohol | 3.600 |
| PEG-40 Castor Oil | 0.600 |
| Ceteareth-20 | 0.500 |
| Sodium cetaryl sulfate | 0.300 |
| Etidronic acid | 0.240 |
| Potassium hydroxide | 0.137 |
| 2,6-Dicarboxypyridine | 0.100 |
| Disodium pyrophosphate | 0.100 |
| Sodium sulfate | 0.0130 |
| Water, demineralized (Aqua) | 72.910 |
| | 100.000 |

TABLE 5

| Blond booster No. 1 (M3) | |
|---|---|
| Potassium persulfate | 97.60 |
| Silica | 1.90 |
| Potassium sulfate | 0.50 |

TABLE 6

| Blond booster No. 2 (M3) | |
|---|---|
| Potassium persulfate | 42.00 |
| Sodium persulfate | 15.40 |
| Ammonium persulfate | 12.80 |
| Sodium silicate | 23.20 |
| Water, demineralized (Aqua) | 4.80 |
| Disodium EDTA | 0.60 |
| Paraffinum Liquidum (mineral oil) | 0.60 |
| Silica | 0.32 |
| Potassium sulfate | 0.20 |
| Ammonium sulfate | 0.06 |
| Sodium sulfate | 0.02 |
| | 100.00 |

Preparation of the Hair Lightening Agents Ready for Use

Hair Lightener No. 1

The alkalizing component according to Table 1 was mixed with the oxidizer preparation (M2) according to Table 4 and the blond booster (M3) according to Table 6 in the mixing ratio 50:50:20 by weight ((M1):(M2):(M3).

The obtained hair lightening agent No. 1 has the following properties:

Viscosity: 28,700 mPas (Brookfield viscometer RDV-II+; 20° C.; spindle 5; 4 RPM) pH value: 10.07 (20° C.)

Hair Lightener No. 2

The alkalizing component according to Table 2 was mixed with the oxidizer preparation (M2) according to Table 4 and the blond booster (M3) according to Table 5 in the mixing ratio 60:60:10 by weight.

The obtained hair lightening agent No. 2 has the following properties:

Viscosity: 23,500 mPas (Brookfield viscometer RDV-II+; 20° C.; spindle 5; 4 RPM)

pH value: 9.95 (20° C.)

Hair Lightener No. 3

The alkalizing component according to Table 3 was mixed with the oxidizer preparation (M2) according to Table 4 and the blond booster (M3) according to Table 6 in the mixing ratio 50:50:20 by weight.

The obtained hair lightening agent No. 3 has the following properties:

Viscosity: 27,000 mPas (Brookfield viscometer RDV-II+; 20° C.; spindle 5; 4 RPM)

pH value: 9.97 (20° C.)

Application

The ready-to-use hair lightening agents No. 1, No. 2 or No. 3 were each applied to the dry hair to be lightened and rinsed out with water after an exposure time of 30-45 minutes. The hair was still cleaned with a shampoo, if desired, washed out again, retreated with a conditioner, washed out again, dried with a towel and then blow-dried at 35-80° C.

With Hair Lightening Agent No. 1 as contemplated herein, a lightening of the hair by 9 color tone levels was achieved ("high lift").

With Hair Lightening Agent No. 2 as contemplated herein, a lightening of the hair by 7 color tone levels was achieved.

With Hair Lightening Agent No. 3 as contemplated herein, a lightening of the hair by 8 color tone levels was achieved.

Improvement of the consistency of the application mixture as well as the homogeneity and the color tone of the whitening result due to the alkalizing component as contemplated herein.

TABLE 7

| Alkalizing component (M1) | | |
|---|---|---|
| | (M1)-E (see Tab. 3) | (M1) - comparison |
| Xanthan gum | 1.500 | 0.000 |
| Cellulose Gum (Carboxymethylcellulose, Sodium Salt) | 0.900 | 0.000 |
| Cetearyl alcohol | 0.000 | 5.750 |
| Coconut fatty alcohol | 0.000 | 2.700 |
| 2-Octyldodecanol | 4.520 | 0.000 |
| Ammonium hydroxide ($NH_4OH$) | 3.900 | 3.900 |
| Ammonium sulfate ($(NH_4)_2SO_4$) | 0.500 | 0.500 |
| Potassium hydroxide | 0.000 | 0.500 |
| Etidronic acid | 0.120 | 0.120 |
| Sodium laureth sulfate (2 EO) | 0.810 | 1.620 |
| Ceteareth-20 | 0.000 | 0.250 |
| Bis-Cetearyl Amodimethicone | 1.000 | 1.000 |
| Sodium Gluceptate (Sodium Heptagluconate) | 1.050 | 0.000 |
| Sodium silicate | 0.000 | 0.190 |
| CI 77007 (ultramarine blue) | 0.100 | 0.100 |
| Perfume | 0.400 | 0.400 |
| Water, demineralized (Aqua) | 85.200 | 82.970 |
| | 100.000 | 100.000 |

Hair Lightening Agent No. 4 as Contemplated Herein

The alkalizing component (M1)-E as contemplated herein as shown in Table 3 and Table 7, respectively, was mixed with the oxidizing agent preparation (M2) as shown in Table 4 and the blond booster (M3) as shown in Table 6 in the mixing ratio 50:50:20 by weight.

Comparative Hair Lightening Agent No. 5 (not as Contemplated Herein)

The alkalizing component (M1)-comparison not as contemplated herein according to Table 7—was mixed with the oxidizing agent preparation (M2) according to Table 4 and the blond booster (M3) according to Table 6 in the mixing ratio 50:50:20 by weight.

Application

The ready-to-use hair lightening agents No. 4 or No. 5 (not as contemplated herein) were applied to the dry hair of 3 test subjects each.

The exposure time to the hair in the attachment area was 40 minutes.

The exposure time to the hair in the length area was 5 minutes.

After the exposure time, the lightening agent was rinsed out of the hair with water. The hair was towel dried and then blow dried at 40° C.

The assessment was made by trained hairdressers for each criterion mentioned in the table below on a grading scale from 1 to 6, where 1 means "poor" and 6 means "excellent".

| Hair Lightening Agent No. 4 (as contemplated herein) | | Test person 1 | 2 | 3 | Arithmetic mean |
|---|---|---|---|---|---|
| Assessment after application | Simplicity of mixing | 5 | 5 | 5 | 5.00 |
| | Skin irritation (before application) | 5 | 5 | 5 | 5.00 |
| | Skin irritation (after application) | 5 | 5 | 5 | 5.00 |
| | Consistency of the application mixture | 5 | 5 | 5 | 5.00 |
| | Simplicity of the application | 5 | 5 | 5 | 5.00 |
| | Hair feel of the dry hair | 4 | 5 | 5 | 4.67 |
| | achieved whitening | 5 | 5 | 5 | 5.33 |
| | Achieved color direction | 5 | 5 | 6 | 5.00 |
| | Level of lightening ("lift") | 5 | 5 | 5 | 5.00 |
| | Uniformity of lightening | 5 | 5 | 6 | 5.33 |
| | Gloss | 5 | 5 | 5 | 5.00 |
| | Scalp feeling | 5 | 5 | 5 | 5.00 |
| | Conclusion | OK | OK | OK | |

| Hair Lightening Agent No. 5 (Comparison, not as contemplated herein) | | Test person 1 | 2 | 3 | Arithmetic mean |
|---|---|---|---|---|---|
| Assessment after application | Simplicity of mixing | 5 | 5 | 5 | 5.00 |
| | Skin irritation (before application) | 5 | 5 | 5 | 5.00 |
| | Skin irritation (after application) | 5 | 5 | 5 | 5.00 |
| | Consistency of the application mixture | 5 | 5 | 5 | 5.00 |
| | Simplicity of the application | 5 | 5 | 5 | 5.00 |
| | Hair feel of the dry hair | 4 | 5 | 5 | 4.67 |
| | achieved whitening | 5 | 5 | 5 | 5.00 |
| | Achieved color direction | 5 | 5 | 6 | 5.33 |
| | Level of lightening ("lift") | 5 | 5 | 5 | 5.00 |
| | Uniformity of lightening | 4 | 5 | 5 | 4.67 |
| | Gloss | 5 | 5 | 5 | 5.00 |
| | Scalp feeling | 5 | 5 | 5 | 5.00 |
| | Conclusion | OK | OK | OK | |

With the alkalizing component as contemplated herein, a better uniformity of the lightening is achieved than with the comparative composition, thus the lightening agent as contemplated herein exhibits a better leveling capacity.

Improvement of the Color Depth of the Whitening Result by the Alkalizing Component as Contemplated Herein

TABLE 8

| Alkalizing component (M1) | (M1)-E (see Tab. 1) | (M1) - comparison |
|---|---|---|
| Xanthan gum | 1.500 | 0.000 |
| Cellulose Gum (Carboxymethylcellulose, Sodium Salt) | 0.900 | 0.000 |
| Cetearyl alcohol | 0.000 | 5.750 |
| Coconut fatty alcohol | 0.000 | 2.700 |
| 2-Octyldodecanol | 4.520 | 0.000 |
| Ammonium hydroxide ($NH_4OH$) | 3.900 | 3.900 |
| Ammonium sulfate ($(NH_4)_2SO_4$) | 0.500 | 0.500 |
| Potassium hydroxide | 0.000 | 0.500 |
| Etidronic acid | 0.120 | 0.120 |
| Sodium laureth sulfate (2 EO) | 0.810 | 1.620 |
| Ceteareth-20 | 0.000 | 0.250 |
| Bis-Cetearyl Amodimethicone | 1.000 | 1.000 |
| Monoethanolamines (2-aminoethanol) | 2.000 | 2.000 |
| Sodium Gluceptate (Sodium Heptagluconate) | 1.050 | 0.000 |
| Sodium silicate | 0.000 | 0.190 |
| CI 77007 (ultramarine blue) | 0.100 | 0.100 |
| Perfume | 0.400 | 0.400 |
| Water, demineralized (Aqua) | 85.200 | 82.970 |
| | 100.000 | 100.000 |

Hair Lightening Agent No. 6 as Contemplated Herein

The alkalizing component (M1)-E as contemplated herein as shown in Table 1 and Table 8, respectively, was mixed with the oxidizing agent preparation (M2) as shown in Table 4 and the blond booster (M3) as shown in Table 6 in the mixing ratio 50:50:20 by weight.

Comparative Hair Lightening Agent No. 7 (not as Contemplated Herein)

The alkalizing component (M1)-comparison not as contemplated herein according to Table 8—was mixed with the oxidizing agent preparation (M2) according to Table 4 and the blond booster (M3) according to Table 6 in the mixing ratio 50:50:20 by weight.

Application

The ready-to-use hair lightening agents No. 6 or No. 7 (not as contemplated herein) were applied to the dry hair of 3 test subjects each.

The exposure time to the hair in the attachment area was 40 minutes.

The exposure time to the hair in the length area was 5 minutes.

After the exposure time, the lightening agent was rinsed out of the hair with water. The hair was towel dried and then blow dried at 40° C.

The assessment was made by trained hairdressers for each criterion mentioned in the table below on a grading scale from 1 to 6, where 1 means "poor" and 6 means "excellent".

| Hair Lightening Agent No. 6 (as contemplated herein) | | Test person 1 | 2 | 3 | Arithmetic mean |
|---|---|---|---|---|---|
| Assessment after application | Simplicity of mixing | 5 | 5 | 5 | 5.00 |
| | Skin irritation (before application) | 5 | 5 | 5 | 5.00 |
| | Skin irritation (after application) | 5 | 5 | 5 | 5.00 |
| | Consistency of the application mixture | 5 | 5 | 5 | 5.00 |
| | Simplicity of the application | 5 | 5 | 5 | 5.00 |
| | Hair feel of the dry hair | 4 | 5 | 5 | 5.00 |
| | achieved whitening | 5 | 5 | 5 | 5.00 |
| | Color depth achieved | 5 | 5 | 6 | 5.33 |
| | Level of lightening ("lift") | 5 | 5 | 5 | 5.00 |
| | Uniformity of lightening | 5 | 5 | 6 | 5.00 |
| | Gloss | 5 | 5 | 5 | 5.00 |
| | Scalp feeling | 5 | 5 | 5 | 5.00 |
| | Conclusion | OK | OK | OK | |

| Hair Lightening Agent No. 7 (Comparison, not as contemplated herein) | | Test person 1 | 2 | 3 | Arithmetic mean |
|---|---|---|---|---|---|
| Assessment after application | Simplicity of mixing | 5 | 5 | 5 | 5.00 |
| | Skin irritation (before application) | 5 | 5 | 5 | 5.00 |
| | Skin irritation (after application) | 5 | 5 | 5 | 5.00 |
| | Consistency of the application mixture | 5 | 5 | 5 | 5.00 |
| | Simplicity of the application | 5 | 5 | 5 | 5.00 |
| | Hair feel of the dry hair | 4 | 5 | 5 | 5.00 |
| | achieved whitening | 5 | 5 | 5 | 5.00 |
| | Color depth achieved | 5 | 5 | 6 | 5.00 |
| | Level of lightening ("lift") | 5 | 5 | 5 | 5.00 |
| | Uniformity of lightening | 4 | 5 | 5 | 5.00 |
| | Gloss | 5 | 5 | 5 | 5.00 |
| | Scalp feeling | 5 | 5 | 5 | 5.00 |
| | Conclusion | OK | OK | OK | |

With the alkalizing component as contemplated herein, a better color depth of the lightening is achieved than with the comparative composition.

The improved spread ability of the application mixture with the alkalizing component as contemplated herein on the hair can also be demonstrated by applying both application mixtures (with the alkalizing component as contemplated herein or with the comparative alkalizing component (M1)) to a glass plate and placing it at a slight angle. The comparative application mixture slides down the plate in one piece, while the application mixture comprising the alkalizing component of the present disclosure spreads across the plate.

Tests on Swelling of the Application Mixture During Prolonged Storage 30 ml each of Hair Lightening Agent No. 6 as contemplated herein and Hair Lightening Agent No. 7 not as contemplated herein were added to a 250 ml measuring cylinder. The volume increase of the hair lightening agents was documented over 45 minutes, see Table 9:

TABLE 9

Volume change of hair lightening agents

| Time [min] | Volume of hair lightening agent as contemplated herein No. 6 [ml]. | Volume hair lightener No. 7 (comparison) [ml]. |
|---|---|---|
| 0 | 30 | 30 |
| 10 | 32 | 32 |
| 15 | 34 | 36 |
| 20 | 34 | 40 |
| 30 | 38 | 44 |
| 40 | 40 | 46 |
| 45 | 42 | 48 |

The application mixture with the alkalizing component (M1) as contemplated herein shows a lower increase in volume during—contrary to instructions—long-term storage than the comparative alkalizing component (M1). This increases the safety of the product for the consumer.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. Alkalizing component for an oxidative hair lightening agent, comprising about 81-92 about wt. % water, about 1-about 2 wt. % xanthan gum, about 0.5-about 1.5 wt. % sodium carboxymethyl cellulose, at least one alkalizing agent chosen from ammonium hydroxide and alkanolamines and mixtures thereof, in a total amount of about 3-about 9 wt. %, at least one oil in a total amount of about 0.5-about 7.0 wt. %, at least one surfactant chosen from anionic, zwitterionic, amphoteric and alkyl oligoglycoside surfactants substituted with at least one C8 to C14 alkyl radical, in a total amount of about 0.4-about 2 wt. %, about 0-about 0.1 wt. % peroxide, where all figures in % by weight are based on the weight of the alkalizing component, wherein the alkalizing component has a pH in the range of about 8.0 to about 12.0 measured at about 20° C., where no percarbonate is present, wherein no polymer or copolymer with acrylate-, methacrylate- or vinyl-containing monomers and no polyurethane is present, and wherein no fat component having a melting point of about 28° C. or higher is included.

2. Alkalizing component according to claim 1, wherein a viscosity is in the range of about 2,000 to about 110,000 mPa-s measured at 20° C.

3. Alkalizing component according to claim 1 wherein no polysaccharide other than xanthan gum and sodium carboxymethylcellulose is present.

4. Alkalizing component according to claim 1, wherein the alkanolamine used as alkalizing agent is chosen from primary amines having a $C_2$-$C_6$ alkyl backbone carrying at least one hydroxyl group.

5. An alkalizing component according to claim 1, wherein the at least one oil is chosen from branched, saturated fatty alcohols having 6-30 carbon atoms and from the esters of saturated, linear or branched fatty alcohols having 2-30 carbon atoms with saturated, linear or branched fatty acids having 2-30 carbon atoms, which may be hydroxylated, and mixtures thereof.

6. An alkalizing component according to claim 1, wherein glucoheptonic acid and/or at least one of its physiologically tolerated salts and/or lactones is further present in a total amount of about 0.1 to about 2 wt. % based on the weight of free glucoheptonic acid in relation to the weight of the alkalizing component.

7. Alkalizing component according to claim 1, wherein furthermore at least one aminated silicone is present in a total amount of about 0.1 to about 2 wt. % based on the weight of the alkalizing component.

8. Packing unit (kit-of-parts), comprising-packed separately from each other at least one container (C1) comprising an alkalizing component according to claim 1, and at least one container (C2) comprising an oxidant preparation (M2) which comprises about 40-about 96 wt. % of water and comprises hydrogen peroxide in a total amount of about 0.5 to about 23 wt. % and has a pH value in the range of about 2.0 to about 6.5 measured at about 20° C., wherein the wt. % data for (M2) relate in each case to the weight of the oxidant preparation (M2), and the oxidant preparation (M2) not comprising a polymer or copolymer with acrylate-, methacrylate- or vinyl-containing monomers and not comprising a polyurethane.

9. A packaging unit according to claim 8, wherein the packaging unit further comprises at least one container (C3) comprising a blond booster composition (M3) in powder form, which is free from percarbonates, polymers and copolymers with acrylate-, methacrylate- or vinyl-containing monomers and is free from polyurethanes and which comprises at least one oxidizing agent chosen from inorganic salts of a peroxosulfuric acid in a total amount of about 5-about 100 wt. % based on the weight of the blond booster and from about 0 to about 8 wt. % of water based on the weight of the blond booster.

10. Process for oxidative hair lightening or bleaching, comprising the following process steps:

i) providing an alkalizing component (M1) according to claim 1, ii) providing an oxidant preparation (M2) comprising about 40-about 96 wt. % of water and comprising hydrogen peroxide in a total amount of about 0.5 to about 23 wt. % and has a pH value in the range from about 2.0 to about 6.5 measured at about 20° C., the wt. % data for (M2) relating in each case to the weight of the oxidant preparation (M2), and the oxidant preparation (M2) not comprising a polymer or copolymer with acrylate-, methacrylate- or vinyl-containing monomers and not comprising a polyurethane, iii) mixing the alkalizing component (M1) with the oxidizing agent preparation (M2), in a weight ratio (M1):(M2) in the range of about 1:0.8 to about 1:2.5, directly followed by iv) applying the mixture obtained in step iii) to the hair and leaving this mixture on the hair for a time of about 1 to about 60 minutes, at room temperature and/or at about 30-about 60° C., v) rinsing the hair with water and/or a cleansing composition, and vi) optionally applying an after-treatment agent to the hair and optionally rinsing followed by drying.

11. The process for oxidative hair lightening or bleaching according to claim 10, wherein before mixing the individual components (M1) and (M2), a blond booster composition (M3) in powder form is further provided which is free from percarbonates, polymers and copolymers with acrylate-, methacrylate- or vinyl-containing monomers and is free from polyurethanes and which comprises at least one oxidizing agent chosen from inorganic salts of a peroxosulfuric acid in a total amount of about 5- about 100 wt. % based on the weight of the blond booster, and from about 0 to about 8 wt. % of water based on the weight of the blond booster, then the cosmetic agent (M1) is mixed with the oxidizing agent preparation (M2) and with the blonde booster composition (M3) in a weight ratio (M1): (M2):(M3) that the weight ratio (M1):(M2) is in the range of about 1:0.8 to about 1:2.5 and (M3) is mixed in an amount of about 5-about 25 wt.-% of the blonde booster composition (M3) based on the weight of the total mixture of (M1), (M2) and (M3), immediately afterwards, the mixture thus obtained is applied to the hair and left on the hair for a period of about 1 to about 60 minutes at room temperature and/or at about 30-about 60° C., immediately afterwards the hair is rinsed with water and/or a cleansing composition, and optionally an after-treatment agent is applied to the hair and optionally rinsed out and then dried.

12. Alkalizing component according to claim 1, wherein a viscosity is of from about 40,000 to about 100,000 mPa-s measured at about 20° C.

13. Alkalizing component according to claim 3, wherein a viscosity is of from about 40,000 to about 100,000 mPa-s measured at about 20° C.

14. Alkalizing component according to claim 4, wherein a viscosity is of from about 40,000 to about 100,000 mPa-s measured at about 20° C.

15. Alkalizing component according to claim 1, wherein a viscosity is of from about 70,000 to about 90,000 mPa-s measured at about 20° C.

16. Alkalizing component according to claim 3, wherein a viscosity is of from about 70,000 to about 90,000 mPa-s measured at about 20° C.

17. Alkalizing component according to claim 4, wherein a viscosity is of from about 70,000 to about 90,000 mPa-s measured at about 20° C.

* * * * *